(12) United States Patent
Hamochi

(10) Patent No.: US 8,101,924 B2
(45) Date of Patent: Jan. 24, 2012

(54) OBJECT-POSITIONING DEVICE FOR CHARGED-PARTICLE BEAM SYSTEM

(75) Inventor: Mitsuru Hamochi, Tokyo (JP)

(73) Assignee: JEOL Ltd., Tokyo (JP)

( * ) Notice: Subject to any disclaimer, the term of this patent is extended or adjusted under 35 U.S.C. 154(b) by 297 days.

(21) Appl. No.: 12/623,545

(22) Filed: Nov. 23, 2009

(65) Prior Publication Data

US 2010/0133448 A1    Jun. 3, 2010

(30) Foreign Application Priority Data

Dec. 3, 2008  (JP) .................................. 2008-308845

(51) Int. Cl.
*H01J 37/20* (2006.01)
(52) U.S. Cl. ................................................. 250/442.11
(58) Field of Classification Search ............. 250/440.11, 250/442.11
See application file for complete search history.

(56) References Cited

U.S. PATENT DOCUMENTS

| 4,101,778 | A | * | 7/1978 | von Rauch et al. | ...... 250/441.11 |
| 4,223,224 | A | * | 9/1980 | Rauch | ...... 250/442.11 |
| 4,405,865 | A | * | 9/1983 | Genty et al. | ...... 250/442.11 |
| 7,566,884 | B2 | * | 7/2009 | Deguchi et al. | ...... 250/442.11 |

FOREIGN PATENT DOCUMENTS

JP    2002-124206 A    4/2002

* cited by examiner

*Primary Examiner* — Jack Berman
(74) *Attorney, Agent, or Firm* — The Webb Law Firm

(57) ABSTRACT

An object-positioning device comprises a rod-like object holder inserted in the chamber of a charged-particle beam system for moving the object outside the chamber, a support for slideably supporting at least a part of the side surface of the object holder, thus making the rear end of the holder outside the chamber a free end, and a vibration-absorbing portion mounted on the rear end of the object holder. The vibration-absorbing portion has an operating range in which vibrational frequencies in a translational direction perpendicular to the longitudinal direction of the object holder are absorbed. The natural vibrational frequency of the object holder in the bending mode is included within the operating range of the vibration-absorbing portion.

5 Claims, 4 Drawing Sheets

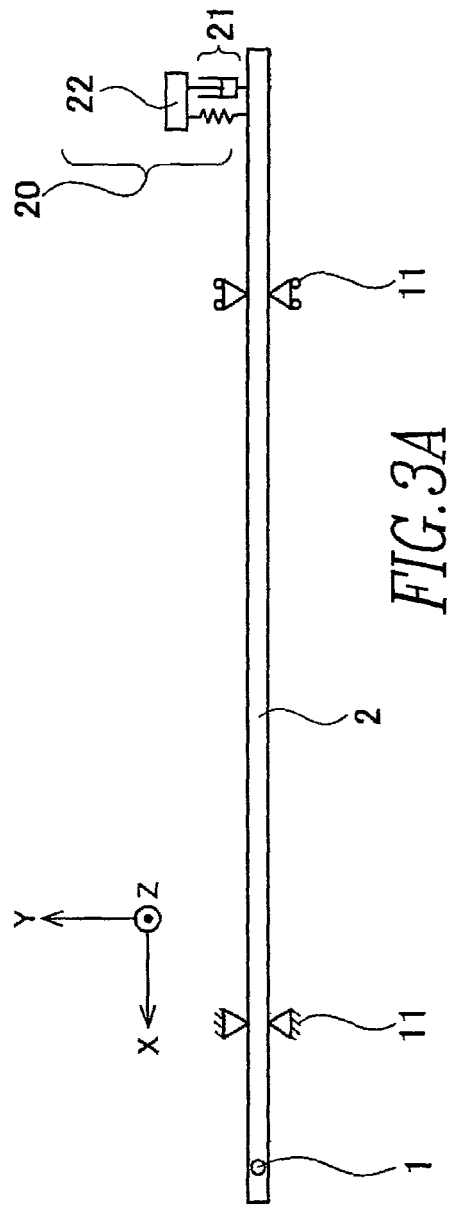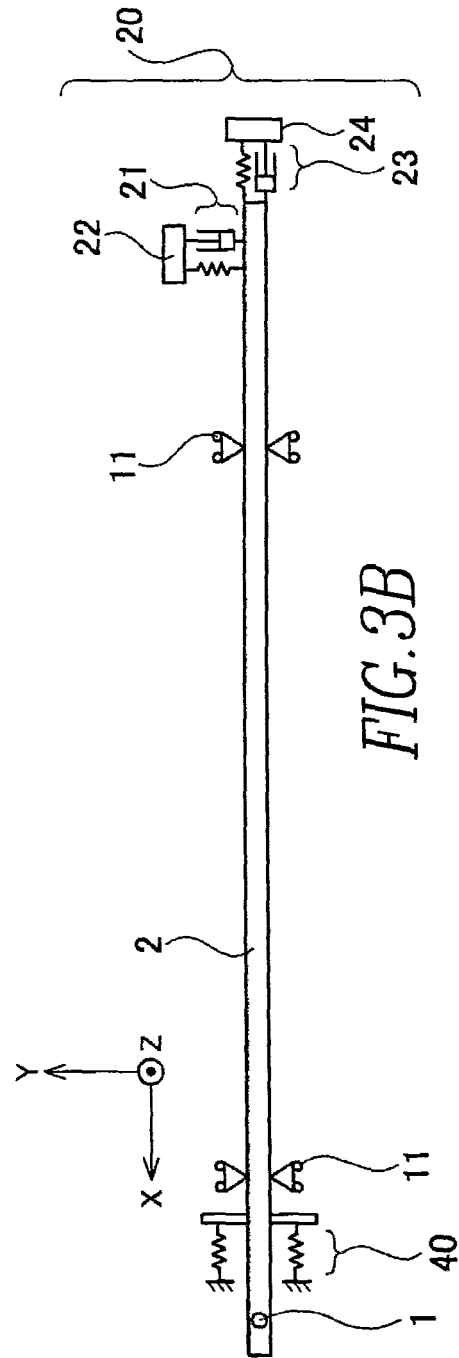

OBJECT-POSITIONING DEVICE FOR CHARGED-PARTICLE BEAM SYSTEM

BACKGROUND OF THE INVENTION

1. Field of the Invention

The present invention relates to an object-positioning device mounted in a charged-particle beam system.

2. Description of Related Art

Mechanical vibrations produced in an analytical instrument or observation instrument using a charged-particle beam (such as an electron microscope) create one of the main factors deteriorating a performance parameter of the instrument such as spatial resolution. Such vibrations are produced by various causes, and examples of the vibrations include vibrations of a building itself, noises around the instrument, and vibrations produced by a machine adjacent to the instrument.

Various portions of the instrument are vibrated from these causes. The natural frequency of each portion of the instrument differs according to shape, material, weight, vibrational mode, and other factors.

A goniometer having a sample holder for holding and moving a sample is disclosed in FIG. 11 of JP-A-2002-124206. In this goniometer, the sample is attached to the front end of the sample holder. A control knob is coupled to the rear end of the holder. The sample holder is slidably inserted in a holder-mounting member, which, in turn, is inserted in a rotary member. The holder is held by a pressure member and screws mounted on the side surface of the rotary member.

A vibration-absorbing member in the form of a hollow disk is mounted at the joint between the control knob and the sample holder to suppress vibrations in the direction of insertion of the sample holder. The vibration-absorbing member is biased toward the control knob by a compression spring via an inertial member. When the sample holder vibrates in the direction of insertion, relative vibrations occur between the sample holder and the inertial member that is inertially at rest. At this time, the vibration-absorbing member deforms (i.e., elongates and shrinks) and converts the vibrational energy into thermal energy. Therefore, vibrations of the sample holder are suppressed.

A vibration suppressor is mounted at the rear end surface of the holder-mounting member in which a compression spring is mounted. The vibration suppressor has a rod standing upright (in the heightwise direction) from the rear end surface, a vibration-absorbing member mounted at the front-end surface of the rod, and an inertial member mounted at the outer surface of the vibration-absorbing member. That is, the vibration-absorbing member is mounted between the rod and the inertial member. If the rod vibrates in the heightwise direction of the rod, relative vibrations are produced between the rod and the inertial member that is inertially at rest. At this time, the vibration-absorbing member expands and contracts and converts the vibrational energy into thermal energy. Accordingly, vibrations of the rod are suppressed. A similar vibration suppressor is mounted on the side surface of the rotary member.

In this way, in the goniometer of JP-A-2002-124206, each of the sample holder and holder-mounting member has a separate vibration-absorbing member.

FIG. 10 of JP-A-2002-124206 shows a movable aperture device that is mounted at the side surface of the electron optical column of a microscopic analysis instrument. The diameter and position of the electron beam are controlled with the aperture. The movable aperture device has an outer spherical ball bearing whose inner surface is formed spherically, a rotatable cylinder, and a holder-mounting member inserted in the rotatable cylinder. The movable cylinder has an inner spherical bearing at its end closer to the electron optical column, the spherical bearing being formed spherically in conformity with the inner surface of the outer spherical bearing. An aperture holder is mounted at the front end of the holder-mounting member. The rotatable cylinder is supported so as to be rotatable about the center of the spherical surfaces of the outer and inner bearings by contact between the bearings.

A feed screw is coupled to the rear end of the holder-mounting member and threadedly engaged in a rotation control member. The feed screw and holder-mounting member are moved longitudinally by rotation of the rotation control member.

The rotation control member has an enlarged portion whose outer surface is covered with a vibration-absorbing member. An annular inertial member consisting of two semi-annular parts interconnected is mounted on the outside of the vibration-absorbing member.

In this movable aperture device, the rotation control member, vibration-absorbing member, and inertial member together constitute a vibration absorber. The principle of vibration absorption is the same as the principle of operation of the vibration absorber of the aforementioned goniometer. When the movable aperture device vibrates around the center of rotation as if it rocks, relative vibrations occur between the rotation control member and the inertial member. Accordingly, the vibration-absorbing member interposed between them expands and shrinks. As a result, the vibrational energy is converted into thermal energy in the vibration-absorbing member. That is, oscillating motion of the vibration absorber is suppressed by this energy conversion.

As described previously, the natural vibrational frequency of each part of the instrument varies depending on shape, material, weight, vibrational mode, and other factors.

Accordingly, in the above-described prior art, each of the sample holder and devices touching the holder is equipped with a vibration suppressor according to the natural vibrational frequency. Therefore, each vibration suppressor needs to be adjusted separately. Also, the structure of the instrument is complicated.

Apart from the method described above, it is conceivable to fabricate the sample holder from a damping alloy. However, the spatial resolution of electron microscopes reaches 0.05 nm. Therefore, the amplitudes of tolerated vibrations of sample are smaller than this value. Furthermore, generally, the damping characteristics of damping alloys deteriorate steeply in a low-strain region. Accordingly, in a strain region created by vibrations smaller than atomic sizes, damping alloys may not exhibit their damping characteristics. In addition, damping alloys are expensive and increase the manufacturing cost.

SUMMARY OF THE INVENTION

It is an object of the present invention to provide an object-positioning device which suppresses very small vibrations by a simple assembly and thus improves the spatial resolution of a charged-particle beam system such as an electron microscope.

One embodiment of the present invention provides an object-positioning device which is for use in a charged-particle beam system and which has a cylindrical and rod-like object holder for holding an object capable of being removably inserted in the charged-particle beam system, support means supporting at least a part of a side surface of the object holder such that the holder can slide, and a vibration-absorbing portion mounted at the rear end (atmospheric side) of the object holder and absorbing vibrations of the object holder. The object holder moves the object from the atmospheric side. The support means makes the rear end (atmospheric side) of the object holder a free end. The object holder shows a natural vibrational frequency in its bending mode. The vibration-absorbing portion operates to absorb vibrations in a frequency range of vibrational frequencies in a translational direction of the vibration-absorbing portion perpendicular to the longitudinal direction of the object holder. The natural vibrational frequency of the object holder lies within the frequency range of operation of the vibration-absorbing portion.

Preferably, the vibration-absorbing portion of the above-described object-positioning device has a first vibration-suppressing member and a first cylindrical inertial member. The inner surface of the first vibration-suppressing member is shaped to contact the side surface of the object holder and shaped cylindrically or as plural box-like members.

Preferably, the first vibration-suppressing member is made of a viscoelastic material having a large loss coefficient to widen the frequency range of operation of the vibration-absorbing portion.

In the object-positioning device described above, the vibration-absorbing portion preferably further includes a second vibration-suppressing member touching the rear end surface of the rod-like object holder and a second inertial member mounted on the outer surface of the second vibration-suppressing member. In this structure, the natural vibrational frequency of the object holder in the translational mode in the longitudinal direction lies within the frequency range of operation of the vibration-absorbing portion in the longitudinal direction of the object holder.

Preferably, the second vibration-suppressing member is made of a viscoelastic material having a large loss coefficient to widen the frequency range of operation of the vibration-absorbing portion.

According to the present invention, vibrations of the sample in the directions of the various axes are suppressed. This improves the spatial resolution of a transmission electron microscope. The vibration-suppressing portion mounted on the end (atmospheric side) of the sample holder directly suppresses vibrations of the holder and so the structure is simplified. Also, the manufacturing cost can be suppressed.

Other objects and features of the invention will appear in the course of the description thereof, which follows.

BRIEF DESCRIPTION OF THE DRAWINGS

FIG. 3A is an equivalent model diagram of the sample holder shown in FIG. 1, illustrating an equivalent model used in analysis of vibrations of a sample holder associated with one embodiment of the present invention;

FIG. 3B is a diagram similar to FIG. 3A but showing the sample holder shown in FIG. 2;

DESCRIPTION OF THE PREFERRED EMBODIMENTS

An embodiment of the present invention is described with reference to the accompanying drawings. An object-positioning device of the present embodiment that is described below is assumed to be mounted in an electron microscope, such as a transmission electron microscope, and to be used as a sample-positioning device that moves the sample. However, the object-positioning device of the present invention can be applied to a mechanism for use with any analysis instrument or observation instrument using a charged-particle beam to move an object over very short distances. The moved object is not limited to a sample. For example, the moved object includes a slit, an aperture, and so on.

Figure 1:
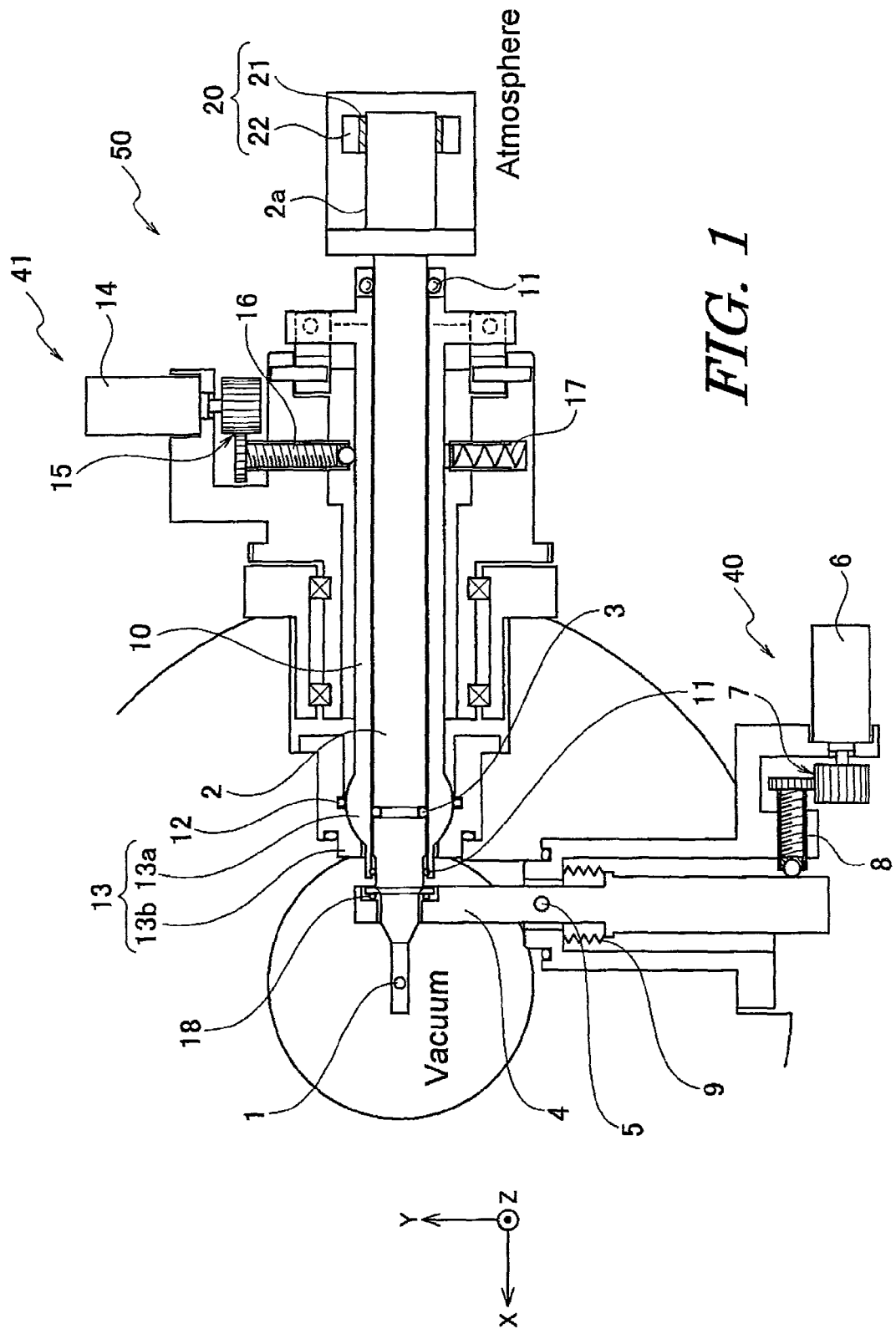
FIG. 1 is a schematic view of one example of a sample-positioning device associated with one embodiment of the present invention.

FIG. 1 is a schematic view of a sample-positioning device associated with one embodiment of the present invention. In this figure, it is assumed that an electron beam (not shown) travels through a vacuum substantially parallel to the Z-axis and passes through a sample 1. The sample-positioning device, generally indicated by 50, is a four-axis positioning device that can move the sample 1 straight along the X-, Y-, and Z-axes and tilt the sample around the X-axis.

A sample holder (object holder) 2 holding the sample 1 is shaped like a cylindrical rod and extends across the partition between the vacuum portion where the sample 1 is placed and the atmospheric portion. The holder 2 is supported by bearings (support means) 11 so as to be slidable and rotatable. The bearings 11 are mounted between the side surface of the holder 2 and a shifter 10 (described later). Both ends of the sample holder 2 can be regarded as free ends. An O-ring 3 is inserted between the side surface of the sample holder 2 and the shifter 10 to hermetically isolate the vacuum portion and the atmospheric portion from each other.

A lever 4 supports and locks the sample 1 in the X-axis direction while preventing the sample holder 2 from being pulled in by the atmospheric pressure. An X-translational mechanism 40 consisting of an X-axis motor 6, a pair of spur gears 7, and an X-axis feed screw 8 is mounted at the rear end of the lever 4. The lever 4 is rotated about its center of rotation 5 by the X-translational mechanism 40. In particular, the X-axis feed screw 8 is moved in the X-axis direction by rotation of the X-axis motor 6. Concomitantly, the sample 1 is moved straight via the lever 4 in the X-axis direction. A bellows 9 maintains the vacuum and smoothens motion of the lever 4. A bearing 18 rotating within the Y-Z plane is mounted at the joint between the sample holder 2 and the lever 4. Consequently, motion in the Y-axis direction is smoothened.

The shifter 10 is shaped cylindrically and provided with a hole extending through it in the X-axis direction. The sample holder 2 is accommodated in this hole. This limits translational motions in the Y-axis and Z-axis directions. That is, the sample holder 2 can move only in the X-axis direction. The aforementioned bearings 11 are mounted near both ends of the hole in the shifter 10 to smoothen motion of the sample holder 2 in the X-axis direction. The positions and number of the bearings 11 are not limited to the example shown in FIG. 1. The positions and number of the bearings 11 can be set at will as long as the sample holder 2 is allowed to move straight and their ends on the atmospheric side are free ends.

The outer surface of the shifter 10 on the sample side is shaped spherically about the axis of center (not shown) of the shifter 10, and forms an inner spherical bearing portion 13a of a spherical bearing 13. The spherical bearing 13 also includes an outer spherical bearing portion 13b whose inner surface makes a sliding contact with the spherical surface of the inner spherical bearing portion 13a. An O-ring 12 for holding the vacuum is mounted between the inner spherical bearing portion 13a and the outer spherical bearing portion 13b. As a result, the shifter 10 can rotate about the center of the spherical bearing 13.

A Y-translational mechanism 41 consisting of a Y-axis motor 14, a pair of spur gears 15, a Y-axis feed screw 16, and a return spring 17 is mounted on the outer surface of the shifter 10 on the atmospheric side. The front end of the Y-axis feed screw 16 is in contact with the side surface of the shifter 10. The side surface of the shifter 10 on the opposite side is biased toward the Y-axis feed screw 16 by the return spring 17. When the Y-axis feed screw 16 is moved in the Y-axis direction by rotation of the Y-axis motor 14, the shifter 10 rotates about the center of the spherical bearing 13. Consequently, the sample 1 is moved straight within a quite small range in the Y-axis direction.

A Z-translational mechanism (not shown) is mounted to translate the sample 1 in the Z-axis direction. Since the Z-translational mechanism is similar in structure to the Y-translational mechanism 41, its description is omitted. Also, description of a mechanism for tilting the sample 1 around the X-axis is omitted.

A vibration-absorbing portion 20 for absorbing vibrations of the sample holder 2 is mounted at the rear end of the sample holder 2 on the atmospheric side. The vibration-absorbing portion 20 has a vibration-suppressing member 21 and an inertial member (weight) 22. Vibrations having frequencies higher than a given vibrational frequency are attenuated if the spring constant of the vibration-suppressing member 21 and the mass of the inertial member 22 are adjusted. Especially, the translational natural vibrational frequency of the vibration-absorbing portion 20 in the Y-axis direction is preferably close to the natural vibrational frequency in the bending mode of the sample holder 2.

The vibration-suppressing member 21 is shaped cylindrically or made of plural box-like portions. The inner surface of the vibration-suppressing member 21 is in contact with the rear side surface 2a such that vibrations of the sample holder 2 are directly transmitted. The vibration-suppressing member 21 is made of a viscoelastic material having a high loss coefficient to widen the frequency range of operation of the vibration-absorbing portion.

As an example, it is assumed that the vibration-suppressing member 21 has a complex rigidity k* (having a real component of k) and a loss coefficient η. The vibration-suppressing member 21 satisfies a relationship given by $$k^* = k(1 + i\eta) \quad (1)$$

On the other hand, when the sample holder 2 vibrates at an amplitude X at a natural angular frequency ω, the force F applied to the sample holder 2 by the vibration-absorbing portion 20 is given by $$F = -\frac{k^* X m \omega^2}{k^* - m\omega^2} \quad (2)$$

where m is the mass of the inertial member 22. The imaginary components of Eq. (2) represent the magnitude of the force F and the frequency range of operation in which vibrations of the sample holder 2 can be suppressed. As the loss coefficient η increases, the frequency range becomes wider. The vibration-suppressing member 21 used in the present invention preferably has a loss coefficient η equal to or greater than 0.5.

The inertial member 22 is shaped cylindrically. The inner surface of the inertial member 22 is in contact with the outer surface of the vibration-suppressing member 21. The inertial member 22 has such a mass that the inertial member 22 exerts a vibration-absorbing force large enough to absorb vibrations of the sample holder 2 in the bending mode.

The manner in which vibrations are suppressed by the sample-positioning device of the present embodiment is next described. FIG. 3A is an equivalent model diagram of the sample holder 2 and the vibration-absorbing portion 20, the diagram being used in vibrational analysis. In this way, the sample holder 2 can be modeled as a rod-like beam which can rotate about the bearings 11 and which have free ends at opposite ends. The vibration-absorbing portion 20 can be modeled as a resilient support in contact with the side end surface of the sample holder 2.

Figure 4A:
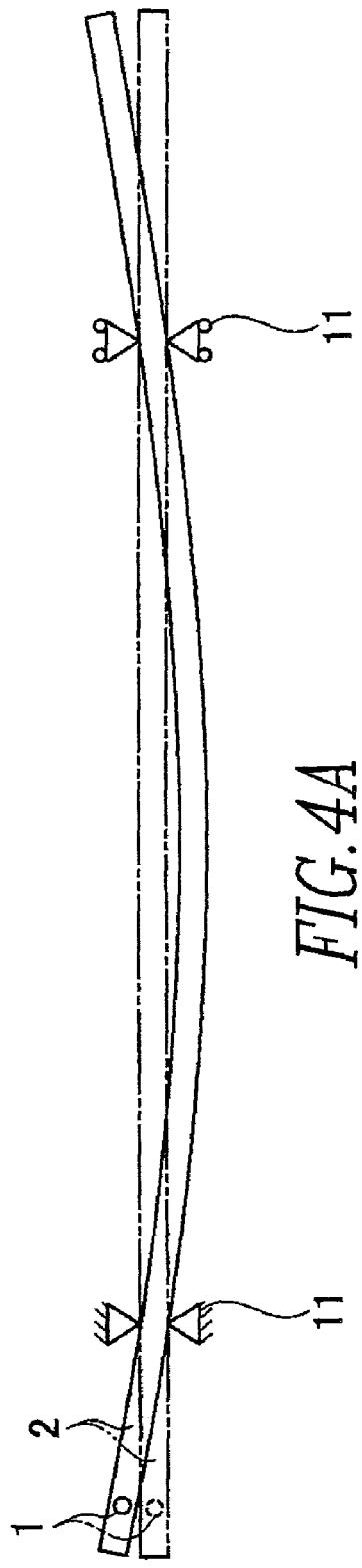
FIG. 4A depicts a bending mode of vibration of a sample holder assumed in the sample-positioning devices shown in FIGS. 1 and 2.

It is assumed that the sample holder 2 vibrates under the condition where the vibration-absorbing portion 20 does not exist. FIG. 4A depicts one example of a bending mode of the modeled sample holder 2. As shown, the opposite ends of the holder 2 are free ends and so the holder vibrates about the bearings 11 in the Y-axis direction.

The vibration-absorbing portion 20 can attenuate the vibrations. For example, where the sample holder 2 produces natural vibrations in the Y-axis direction as shown in FIG. 4A, relative vibrations occur between the ends of the holder 2 and the inertial member 22 because the natural vibrational frequency of the vibration-absorbing portion 20 is close to that of the natural vibrations of the holder 2. The interposed vibration-suppressing member 21 is repeatedly elongated and shrunk. As a result, the inertial member 22 exerts the vibration-absorbing force on the sample holder 2 via the vibration-suppressing member 21. Consequently, the vibrations of the sample holder 2 are suppressed. It can be seen that vibrations in the Z-axis direction can be suppressed because of this principle in the same way as vibrations in the Y-axis direction.

Where the sample holder 2 vibrates in the X-axis direction, if the vibrational frequency is higher than the natural vibrational frequency of the vibration-absorbing portion 20 in the X-axis direction (the vibration-suppressing portion 21 consisting of the mass of the inertial member 22 and the spring constant of the vibration-absorbing member 20 in the shear direction), then the vibration-absorbing force in the X-axis direction acts on the sample holder 2. Consequently, a shear stress occurs across the vibration-suppressing member 21 in the X-axis direction. Variations in the shear stress while the holder is vibrating are converted into thermal energy in the vibration-suppressing member 21. In consequence, vibrations in the sample holder 2 in the X-axis direction are suppressed.

In this way, according to the present invention, vibrations of the sample holder 2 in the bending mode can be suppressed directly at a maximum efficiency by mounting the vibration-absorbing portion 20 on the side surface 2a of the sample holder 2 on the atmospheric side. Because vibrations of the sample 1 in the X-, Y-, and Z-axis directions are suppressed by the method of suppression described above, the spatial resolution of the transmission electron microscope is improved.

Furthermore, in the present invention, vibrations of the sample holder 2 are directly suppressed with the vibration-absorbing portion 20 alone. That is, vibrations of the sample holder 2 giving a direct cause of vibrations of the sample 1 are directly suppressed using only the vibration-absorbing portion 20 on the atmospheric side of the holder 2, unlike the prior art where each component of a charged-particle beam system is fitted with a separate vibration suppressor as shown in JP-A-2002-124206. Hence, the number of components necessary for suppression of vibrations of the sample 1 can be reduced. As a result, the manufacturing cost can be suppressed. In the movable aperture device shown in JP-A-2002-124206, resilient elements are created between a vibration suppressor and a holder-mounting member due to threaded engagement and rattling of a feed screw. In the present invention, such elements do not exist. Therefore, with respect to the vibrational frequencies to be suppressed, it is necessary to take account of only the natural vibrational frequency of the sample holder 2. Adjustment of the attenuating characteristics of the vibration-suppressing member 21 and setting of the mass of the inertial member 22 are facilitated. This also contributes to suppression of manufacturing cost.

Figure 4B:
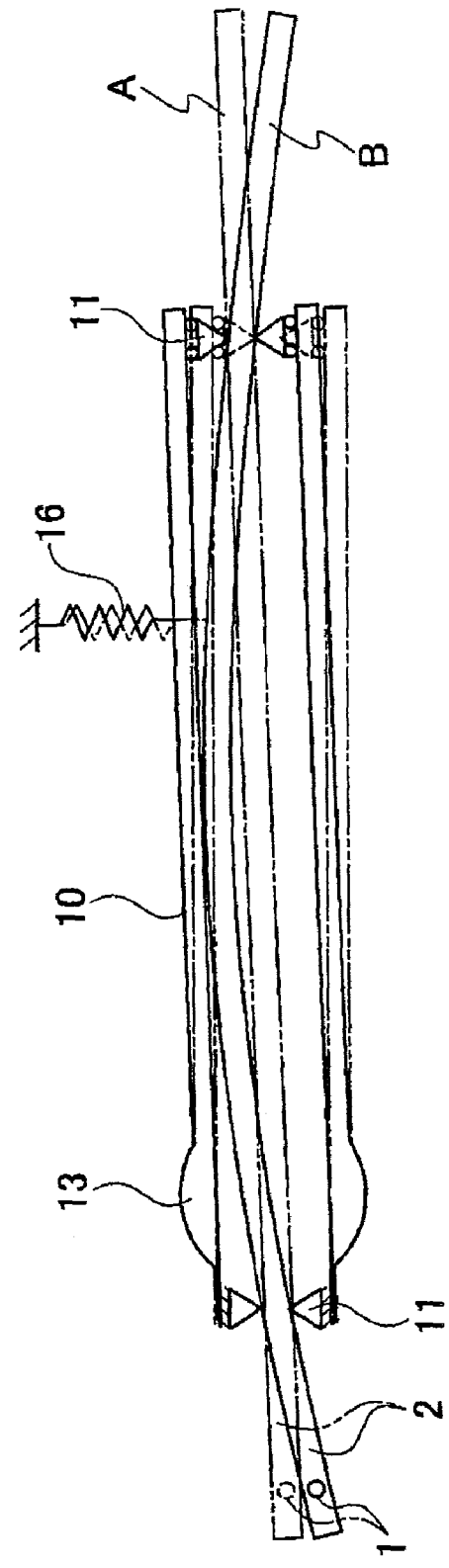
FIG. 4B depicts a rocking mode of vibration of a shifter.

Furthermore, the vibration-absorbing portion 20 associated with the present invention suppresses vibrations of other than the sample holder 2. For example, in some cases, the shifter 10 is swung about the center of the spherical bearing 13 due to noise. This vibrational mode of the shifter 10 is referred to as the rocking mode, which is depicted in FIG. 4B. Rocking mode vibrational frequencies generally induced by noises are generally higher than bending mode vibrational frequencies of the sample holder 2.

Where the sample holder 2 can be regarded as a rigid body, the sample holder 2 rocks about the center of the spherical bearing 13 together with the shifter 10 as indicated by the arrow A. In practice, however, the sample holder 2 is not a rigid body and, therefore, does not move integrally with the shifter 10. The sample holder 2 bends as indicated by the arrow B. Accordingly, vibrations of the sample 1 in the Y-axis direction depend on the bending mode of the sample holder 2, as well as on rocking mode vibrations of the shifter 10.

As described previously, however, the vibration-absorbing portion 20 having a high loss coefficient operates over a wide range of frequencies. Rocking mode frequencies of the shifter 10 are included in this range. Therefore, vibrations due to bending of the sample holder 2 are suppressed by the vibration-absorbing portion 20. The vibration-absorbing portion 20 does not directly suppress the rocking mode of the shifter 10 but can efficiently suppress increases (difference between B and A of FIG. 4B) in vibrations of the sample 1 due to bending of the sample holder 2. Consequently, vibrations of the sample 1 in the rocking mode of the shifter 10 are suppressed.

In this way, in the present invention, vibrations of the sample holder 2 that would eventually lead to vibrations of the sample 1 are absorbed by the vibration-absorbing portion 20. Therefore, vibrations of external devices that are in indirect contact with the sample holder 2 (i.e., in contact via the bearings 11) can also be suppressed.

Suppression of vibrations using a damping alloy makes use of hysteretic damping using the strain of the damping alloy itself. In contrast, the vibration-absorbing portion of the present invention attenuates vibrations by utilizing the operation of the vibration-absorbing force. Accordingly, the vibration-absorbing portion effectively acts on vibrations having amplitudes less than atomic sizes.

(Modification)

Figure 2:
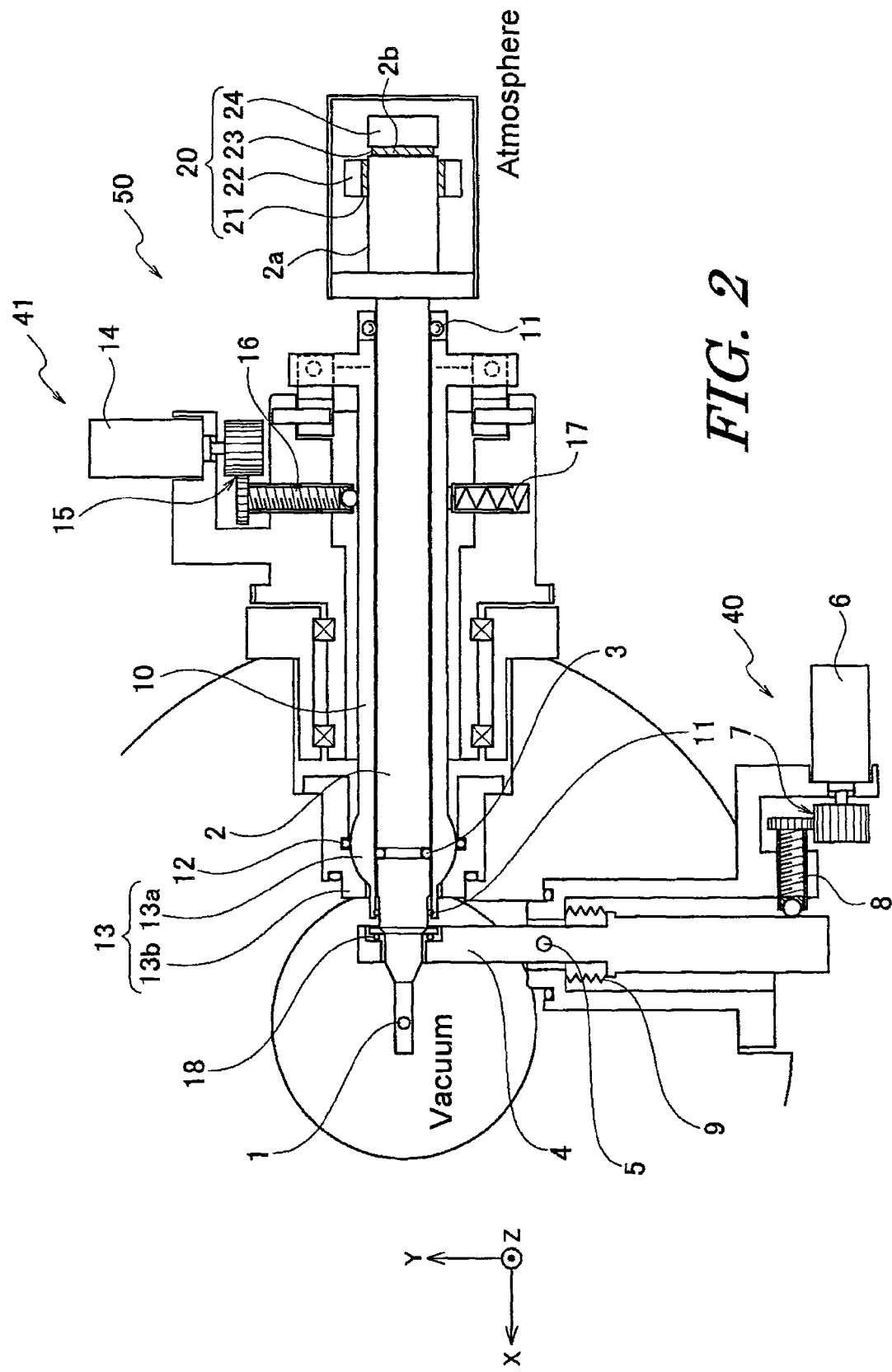
FIG. 2 is a schematic view of a modification of the sample-positioning device shown in FIG. 1.

One modification of the sample-positioning device 50 is described. FIG. 2 schematically depicts this modification. Like components are indicated by like reference numerals in both FIGS. 1 and 2. Those components which have been already described will not be described below.

As shown in FIG. 2, the vibration-absorbing portion 20 has a vibration-suppressing member 23 in contact with the rear end surface 2b of the sample holder 2 and an inertial member (weight) 24 mounted to touch the rear surface of the vibration-suppressing member 23, in addition to the structure shown in FIG. 1. That is, the vibration-suppressing member 23 is sandwiched between the rear end surface 2b of the sample holder 2 and the inertial member 24. FIG. 3B depicts an equivalent model of the sample holder 2 and vibration-absorbing portion 20 of the present modification, the model being used in vibrational analysis. In FIG. 2, the X-translational mechanism 40 is added as a resilient support.

The vibration-suppressing member 23 is made of a viscoelatic material having a large loss coefficient similarly to the vibration-suppressing member 21, in order to suppress vibrations in a wide frequency range. The inertial member 24 has such a mass that the member 24 exerts a sufficiently strong vibration-absorbing force on translational vibrations of the sample holder 2 in the X-axis direction.

In the present modification, the subassembly of the vibration-suppressing member 23 and the inertial member 24 attenuates vibrational frequencies higher than a given value when an adjustment is made with the spring constant of the vibration-suppressing member 23 and the mass of the inertial member 24. In this adjustment, the translational natural vibrational frequency of the subassembly in the X-axis direction is preferably close to the natural vibrational frequency of the sample holder 2 in the translational mode. The natural vibrational frequency of the sample holder 2 in the translational mode depends on the mass of the sample holder 2 and on the X-axis component of the spring constant of the whole X-translational mechanism.

When the sample holder 2 vibrates at its natural vibrational frequency in the X-axis direction, the holder 2 and the subassembly of the vibration-suppressing member 23 and the inertial member 24 do not vibrate as a unit, because the natural vibrational frequency of the subassembly in the X-axis direction is close to the natural vibrational frequency of the holder 2. Rather, the vibration-suppressing member 23 is elongated and contracted due to relative vibrations between the sample holder 2 and the inertial member 24. Consequently, a vibration-absorbing force is made to act on the sample holder 2. As a result, vibrations of the holder 2 in the X-axis direction are suppressed.

It can be expected that the combination of the vibration-suppressing member 21 and the inertial member 22 will suppress vibrations of the sample holder 2 in the X-axis direction. In the present modification, the operating frequency range of the subassembly of the vibration-suppressing member 23 and the inertial member 24 is adjusted while taking account of the translational mode natural vibrational frequency of the sample holder 2 in the X-axis direction. Therefore, vibrations of the sample holder 2 in the X-axis direction can be suppressed more effectively. Furthermore, a shearing stress is produced in the vibration-suppressing member 23 because this member 23 is mounted at the rear end surface 2b of the sample holder 2. As a consequence, vibrations of the sample holder 2 in the Y-axis direction, Z-axis direction, and their resultant direction are more suppressed.

Having thus described my invention with the detail and particularity required by the Patent Laws, what is protected by Letters Patent is set forth in the following claims.

The invention claimed is:

1. An object-positioning device for use in a charged-particle beam system, said object-positioning device extending into an evacuateable chamber comprising:

an object holder holding an object capable of being removably inserted in the charged-particle beam system, the object holder being used to manipulate the position of the object from outside the chamber, the object holder being shaped cylindrically or like a rod, the object holder having a rear end outside the chamber, the object holder having a natural vibrational frequency in its bending mode;

support means supporting at least one portion of a side surface of the object holder such that the holder can slide and that the rear end of the object holder is made a free end; and a vibration-absorbing portion mounted to the rear end of the object holder outside the chamber side and acting to absorb vibrations of the object holder, wherein the vibration-absorbing portion has an operating frequency range in which vibrations are absorbed in a translational direction perpendicular to a longitudinal direction of the object holder, and wherein said natural vibrational frequency of the object holder in the bending mode is included within the operating frequency range of the vibration-absorbing portion.

2. An object-positioning device for use in a charged-particle beam system as set forth in claim 1, wherein said vibration-absorbing portion has: a first vibration-suppressing member made of a cylindrical part or a plurality of box-like parts and having an inner surface in contact with an inner surface of the object holder; and a first inertial member mounted on an outer surface of the first vibration-suppressing member.

3. An object-positioning device for use in a charged-particle beam system as set forth in claim 2, wherein said first vibration-suppressing member is made of a viscoelastic material.

4. An object-positioning device for use in a charged-particle beam system as set forth in claim 2 or 3, wherein said vibration-absorbing portion further includes a second vibration-suppressing member in contact with the rear end of the object holder shaped like a rod and a second inertial member mounted on an outer surface of the second vibration-suppressing member, wherein the vibration-absorbing portion has a second operating frequency range in which vibrations in a translational direction of the vibration-absorbing portion are absorbed in a longitudinal direction of the object holder, and wherein said natural vibrational frequency of the object holder in a translational mode in the longitudinal direction of the object holder is included within the second operating frequency range of the vibration-absorbing portion.

5. An object-positioning device for use in a charged-particle beam system as set forth in claim 4, wherein said second vibration-suppressing member is made of a viscoelastic material.

* * * * *